United States Patent
Naik et al.

(10) Patent No.: US 9,000,231 B2
(45) Date of Patent: Apr. 7, 2015

(54) PROCESSES FOR MAKING MAGNOLOL AND DERIVATIVES THEREOF

(75) Inventors: Ramesh Naik, Karnataka (IN); Sanju Walikar, Karnataka (IN); Ramesh Jayaramaiah, Karnataka (IN); Vangumalla Devaki Devi, Karnataka (IN); Govindarajalu Jeyaraman, Karnataka (IN); Koottungalmadhom Ramaswamy Ranganathan, Karnataka (IN)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/365,791

(22) PCT Filed: Jun. 20, 2011

(86) PCT No.: PCT/US2011/066045
§ 371 (c)(1),
(2), (4) Date: Jun. 16, 2014

(87) PCT Pub. No.: WO2013/095361
PCT Pub. Date: Jun. 27, 2013

(65) Prior Publication Data
US 2014/0357902 A1 Dec. 4, 2014

(51) Int. Cl.
| | | |
|---|---|---|
| *C07C 37/50* | (2006.01) |
| *C07C 37/62* | (2006.01) |
| *C07C 41/06* | (2006.01) |
| *C07C 41/22* | (2006.01) |
| *C07C 41/24* | (2006.01) |
| *C07C 37/68* | (2006.01) |
| *C07C 37/00* | (2006.01) |

(52) U.S. Cl.
CPC .................. *C07C 37/50* (2013.01); *C07C 41/06* (2013.01); *C07C 41/22* (2013.01); *C07C 41/24* (2013.01); *C07C 37/68* (2013.01); *C07C 37/003* (2013.01); *C07C 2101/16* (2013.01)

(58) Field of Classification Search
None
See application file for complete search history.

(56) References Cited

U.S. PATENT DOCUMENTS

| 7,608,741 | B2 | 10/2009 | Kim et al. |
| 2008/0039643 | A1 | 2/2008 | Vass et al. |
| 2009/0149402 | A1 | 6/2009 | Miyagi et al. |
| 2010/0056463 | A1 | 3/2010 | Raederstorff et al. |

FOREIGN PATENT DOCUMENTS

| CN | 1270168 A | 10/2000 |
| CN | 101293816 A | 10/2008 |
| EP | 1831144 | 9/2007 |
| WO | WO0185116 | 11/2001 |
| WO | WO2011106003 | 9/2011 |
| WO | WO2011106492 | 9/2011 |
| WO | WO2011106493 | 9/2011 |

OTHER PUBLICATIONS

Database CAPLUS 2012:586918, Zhang et al., Huaxue Yanjiu Yu Yingyong (2011), 23(11), pp. 1574-1576 (abstract).*
International Search Report and the Written Opinion issued in International Application PCT/US2011/066045 mailed Dec. 20, 2011 WO.

(Continued)

*Primary Examiner* — Brian J Davis
(74) *Attorney, Agent, or Firm* — Anne Louise St. Martin

(57) ABSTRACT

Described herein are high yield methods for making magnolol (5,5'-diallyl-biphenyl-2,2'-diol) and tetrahydro-magnolol (5,5'-dipropyl-biphenyl-2,2'-diol).

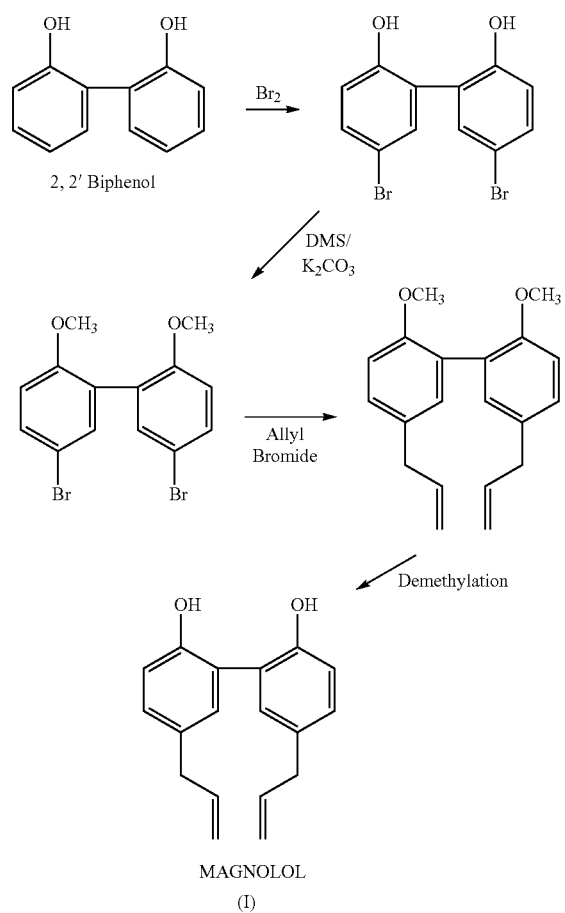

5 Claims, No Drawings

(56) References Cited

OTHER PUBLICATIONS

Written Opinion of the International Preliminary Examining Authority issued in International Application PCT/US2011/066045 mailed Dec. 10, 2013. WO.

Runeberg J: "Phenol Dehydrogenations—VIII. Synthesis of Magnolol," ACTA Chemica Scandinavica, Munksgaard, Copenhagen, DK, vol. 12, Jan. 1, 1958, pp. 188-192, XP002575197, ISSN: 0904-213X, p. 189 scheme, p. 190, paragraph 1-paragraph 5 SE.

* cited by examiner

PROCESSES FOR MAKING MAGNOLOL AND DERIVATIVES THEREOF

CROSS-REFERENCE TO RELATED PATENT APPLICATIONS

The present application is a U.S. national stage entry under 35 U.S.C. §371 of Patent Cooperation Treaty Patent Application No. PCT/US2011/66045, filed Dec. 20, 2011, the entirety of which is incorporated herein by reference.

BACKGROUND

There is a need for safe, effective antibacterial and anti-inflammatory agents for use in oral care compositions. Magnolia extract is known to contain compounds having antibacterial and/or anti-inflammatory properties, and such compounds have been the focus of considerable interest for use in oral care compositions. The use of such compounds in oral care compositions is described, for example, in WO2001/085116, WO 2011/106492 and WO 2011/106493, the contents of which application are incorporated herein by reference. Methods of synthesizing magnolol (5,5'-diallyl-biphenyl-2,2'-diol) are disclosed, e.g. in WO 2011/106003. Synthetic non-natural analogs of various components of magnolia extract having other alkyls in place of allyl are also known to have antibacterial activity, but the compounds are in some cases expensive or difficult to synthesize.

Existing synthetic methods for magnolol involve costly reagents and yields are low. There is a need for cheaper, higher yield synthetic procedures to make magnolol and related compounds.

SUMMARY

Previous synthetic approaches to making magnolol generally start with bromination of biphenyl-2,2'-diol, to get the 5,5'-dibromo-biphenyl-2,2'-diol, followed by O-protection, with methyl or other O-protecting group, reaction with allyl bromide to get the magnolol in protected form, and deprotection to obtain magnolol (5,5'-diallyl-biphenyl-2,2'-diol, sometimes named as 4,4'-diallyl-2,2'biphenol). We have found that on scale up, the step of O-protecting the 5,5'-dibromo-biphenyl-2,2'-diol is inefficient and slow. We have found that carrying out the O-protection step before the bromination step results in a more efficient reaction and higher yields.

The deprotection step is another expensive and yield limiting step in the existing processes. The methods reported for demethylation are often costly, and require sometimes very low temperatures (−78° C. using BBr$_3$) and sometimes reflux conditions. The reaction mixture is always difficult to separate and purify which results in low yield of magnolol. We have found that the use of an aluminium chloride/thiourea complex for deprotection does not require extreme temperatures or expensive reagents and results in high yields.

Some embodiments of the present invention provide a simple, relatively high yield synthesis for magnolol (5,5'-diallyl-biphenyl-2,2'-diol), comprising
  (i) methylating biphenyl-2,2'-diol using dimethyl sulfate, to obtain 2,2'-dimethoxy-biphenyl;
  (ii) brominating the 2,2'-dimethoxy-biphenyl to obtain 2,2'-dimethoxy-5,5'-dibromo-biphenyl;
  (iii) alkylating the 2,2'-dimethoxy-5,5'-dibromo-biphenyl with allyl bromide to obtain 2,2'-dimethoxy-5,5'-diallyl-biphenyl;
  (iv) demethylating the 2,2'-dimethoxy-5,5'-diallyl-biphenyl by reaction with aluminium chloride and thiourea; and
  (v) recovering the 5,5'-diallyl-biphenyl-2,2'-diol thus obtained.

In some embodiments, the present invention further provides a method for production of tetrahydromagnolol (5,5'-dipropyl-biphenyl-2,2'-diol), comprising hydrogenating the 5,5'-diallyl-biphenyl-2,2'-diol product of the foregoing method, e.g., in the presence of a palladium or nickel catalyst.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DETAILED DESCRIPTION

The invention thus provides a method (Method 1) for making magnolol (5,5'-diallyl-biphenyl-2,2'-diol), comprising
  (i) methylating biphenyl-2,2'-diol using dimethyl sulfate, to obtain 2,2'-dimethoxy-biphenyl;
  (ii) brominating the 2,2'-dimethoxy-biphenyl to obtain 2,2'-dimethoxy-5,5'-dibromo-biphenyl;
  (iii) alkylating the 2,2'-dimethoxy-5,5'-dibromo-biphenyl with allyl bromide to obtain 2,2'-dimethoxy-5,5'-diallyl-biphenyl;
  (iv) demethylating the 2,2'-dimethoxy-5,5'-diallyl-biphenyl by reaction with aluminium chloride and thiourea; and
  (v) recovering the 5,5'-diallyl-biphenyl-2,2'-diol thus obtained.

1.1. Method 1 wherein step (i) is carried out in aqueous media in presence of an inorganic base, e.g., sodium hydroxide or potassium hydroxide.
1.2. Any of the foregoing methods wherein step (iii) is carried out in a polar aprotic solvent, e.g., tetrahydrofuran (THF).
1.3. Any of the foregoing methods wherein the demethylation step (iv) is carried out at temperatures between 30° C. and 60° C.

The general reaction scheme is as follows:

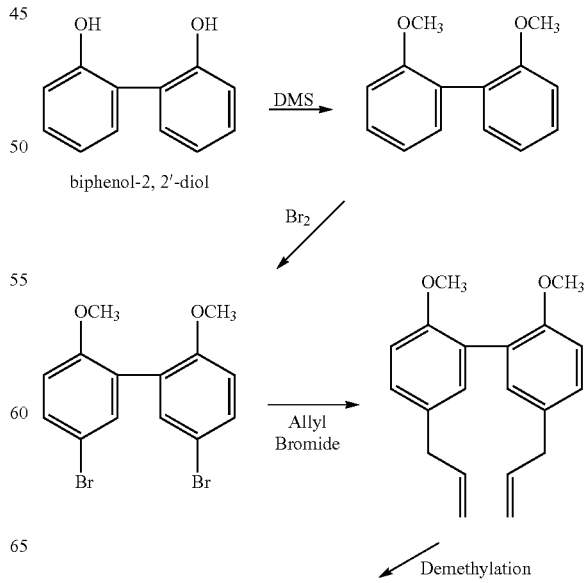

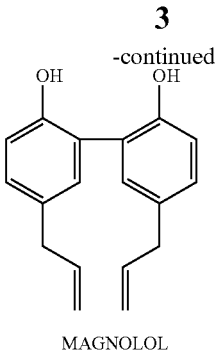

MAGNOLOL

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

EXAMPLE

Example 1

Synthesis of Magnolol
(5,5'-diallyl-biphenyl-2,2'-diol)

2,2'-Biphenol is reacted in sodium hydroxide with dimethyl sulfate for 1-2 hours to give 2,2'-bianisole (95% yield). Solid is separated, washed with water and dried at 60-65° C. 2,2'-bianisole is efficiently brominated to give 4,4'-Dibromo-2,2'-bianisole which is then reacted with allyl bromide in THF to obtain 4,4'-Diallyl-2,2'-bianisole.

The 4,4'-diallyl-2,2'-bianisole is added to a mixture of aluminum chloride, thiourea and 1,2-dichloroethane slowly over 3 hours at 50° C. Temperature and stirring is maintained for an additional 3-4 hours. Reaction mix is cooled and added to HCl and phases are separated. The organic layer is added to charcoal, filtered and the solvent distilled, to obtain the title compound.

The invention claimed is:

1. A method for making magnolol (5,5'-diallyl-biphenyl-2,2'-diol) or tetrahydromagnolol (5,5'-dipropyl-biphenyl-2,2'-diol), comprising
   i) methylating biphenyl-2,2'-diol using dimethyl sulfate, to obtain 2,2'-dimethoxy-biphenyl;
   ii) brominating the 2,2'-dimethoxy-biphenyl to obtain 2,2'-dimethoxy-5,5'-dibromo-biphenyl;
   iii) alkylating the 2,2'-dimethoxy-5,5'-dibromo-biphenyl with allyl bromide to obtain 2,2'-dimethoxy-5,5'-diallyl-biphenyl;
   iv) demethylating the 2,2'-dimethoxy-5,5'-diallyl-biphenyl by reaction with aluminium chloride and thiourea;
   v) recovering the 5,5'-diallyl-biphenyl-2,2'-diol thus obtained; and
   vi) optionally hydrogenating the 5,5'-diallyl-biphenyl-2,2'-diol in the presence of a metal catalyst and recovering the 5,5'-dipropyl-biphenyl-2,2'-diol thus obtained.

2. The method of claim 1 wherein step (i) is carried out in aqueous media in the presence of an inorganic base.

3. The method of claim 1 wherein step (iii) is carried out in a polar aprotic solvent.

4. The method of claim 1 wherein step (iv) is carried out at temperatures between 30° C. and 60° C.

5. The method of claim 1 comprising optional step (vi).

* * * * *

UNITED STATES PATENT AND TRADEMARK OFFICE
CERTIFICATE OF CORRECTION

PATENT NO. : 9,000,231 B2  
APPLICATION NO. : 14/365791  
DATED : April 7, 2015  
INVENTOR(S) : Ramesh Naik et al.

Page 1 of 1

It is certified that error appears in the above-identified patent and that said Letters Patent is hereby corrected as shown below:

On the Title page delete "Jun. 16, 2011" at "(86) § 371 (c)(1), (2), (4) Date:"

add "Dec. 20, 2011" at "(86) § 371 (c)(1), (2), (4) Date:"

Signed and Sealed this  
Twenty-eighth Day of July, 2015

Michelle K. Lee  
*Director of the United States Patent and Trademark Office*